US012026263B2

(12) United States Patent
Lin et al.

(10) Patent No.: US 12,026,263 B2
(45) Date of Patent: Jul. 2, 2024

(54) METHOD AND APPARATUS FOR PROTECTING PRIVACY OF OPHTHALMIC PATIENT AND STORAGE MEDIUM

(71) Applicants: Zhongshan Ophthalmic Center, Sun Yat-Sen University, Guangdong (CN); Tsinghua University, Beijing (CN)

(72) Inventors: Haotian Lin, Guangdong (CN); Feng Xu, Beijing (CN); Yahan Yang, Guangdong (CN); Ruixin Wang, Guangdong (CN); Junfeng Lyu, Beijing (CN)

(73) Assignees: Zhongshan Ophthalmic Center, Sun Yat-Sen University, Guangzhou (CN); Tsinghua University, Beijing (CN)

( * ) Notice: Subject to any disclaimer, the term of this patent is extended or adjusted under 35 U.S.C. 154(b) by 376 days.

(21) Appl. No.: 17/548,486

(22) Filed: Dec. 10, 2021

(65) Prior Publication Data

US 2023/0076853 A1 Mar. 9, 2023

(30) Foreign Application Priority Data

Sep. 3, 2021 (CN) ......................... 202111031513.5

(51) Int. Cl.
*G06T 7/00* (2017.01)
*G06F 21/60* (2013.01)
(Continued)

(52) U.S. Cl.
CPC ................ *G06F 21/60* (2013.01); *G06T 5/70* (2024.01); *G06T 5/73* (2024.01); *G06T 7/0012* (2013.01);
(Continued)

(58) Field of Classification Search
CPC ....... G06F 21/60; G06F 21/6245; G06T 5/70; G06T 5/73; G06T 7/0012; G06T 7/11; G06T 2207/30041; G06T 2207/10016; G06T 2207/20081; G06T 2207/20084; G06T 17/00; G06T 15/005; G06N 3/02; G06N 3/08; G06N 3/04; G16H 10/60; G16H 30/40; G16H 50/20; G16H 50/50; Y02T 10/40
See application file for complete search history.

(56) References Cited

U.S. PATENT DOCUMENTS

2018/0012418 A1* 1/2018 Bêrard .................... G06T 17/00
2018/0360655 A1* 12/2018 Berlin .................... A61B 3/145
(Continued)

*Primary Examiner* — Ping Y Hsieh

(57) ABSTRACT

A method and an apparatus for protecting privacy of an ophthalmic patient and a storage medium are disclosed. The method includes: acquiring an examination video of the ophthalmic patient; extracting image features of each frame of images in the examination video, performing region division on each frame of the images according to position information of organs in the image features, and obtaining a region to be precisely reconstructed and a region to be roughly reconstructed according to a region division result; performing three-dimensional (3D) reconstruction on the region to be precisely reconstructed and the region to be roughly reconstructed, to obtain 3D reconstruction data corresponding to each frame of the images; and rendering all the 3D reconstruction data into a 3D reconstruction video.

13 Claims, 1 Drawing Sheet

Acquire an examination video of an ophthalmic patient — S1

Extract image features of each frame of images in the examination video, perform region division on each frame of the images according to position information of organs in the image features, and obtain a region to be precisely reconstructed and a region to be roughly reconstructed according to a region division result — S2

Perform 3D reconstruction on the region to be precisely reconstructed and the region to be roughly reconstructed, to obtain 3D reconstruction data corresponding to each frame of the images — S3

Render all the 3D reconstruction data into a 3D reconstruction video — S4

(51) Int. Cl.

| | |
|---|---|
| ***G06T 5/70*** | (2024.01) |
| ***G06T 5/73*** | (2024.01) |
| ***G06T 7/11*** | (2017.01) |

(52) U.S. Cl.

CPC ...... *G06T 7/11* (2017.01); *G06T 2207/30041* (2013.01)

(56) References Cited

U.S. PATENT DOCUMENTS

| | | | | |
|---|---|---|---|---|
| 2019/0060602 | A1* | 2/2019 | Tran ........................ | G16H 20/30 |
| 2020/0387706 | A1* | 12/2020 | Zur ........................ | G06T 7/0012 |
| 2021/0335483 | A1* | 10/2021 | Freeman ............ | G02B 21/0012 |
| 2023/0419629 | A1* | 12/2023 | Huang .................... | G06T 7/596 |

* cited by examiner

METHOD AND APPARATUS FOR PROTECTING PRIVACY OF OPHTHALMIC PATIENT AND STORAGE MEDIUM

CROSS REFERENCE TO RELATED APPLICATIONS

The present application claims the benefit of Chinese Patent Application No. 202111031513.5 filed on Sep. 3, 2021, the contents of which are incorporated herein by reference in their entirety.

TECHNICAL FIELD

The present disclosure relates to the technical field of computer graphics, and in particular to, a method and an apparatus for protecting privacy of an ophthalmic patient and a storage medium.

BACKGROUND

With the increasing popularity of digitalization, digital treatment attracts wide attention. Digital treatment is a new approach to integrating an information technology into the whole treatment process. However, digital treatment brings about some problems, for example, how to protect privacy of a patient. How to better protect the privacy of a patient becomes an urgent problem to be resolved. Currently, because facial information digitally shows disease signs, and inevitably reserves sensitive biometric identification information, how to precisely distinguish sensitive biometric identification information from facial information is a major technical difficulty in the field of face privacy protection.

An existing method for protecting the privacy of an ophthalmic patient is mainly to cover a privacy region of an image including identification information. However, in this method, identification information in an uncovered region cannot be removed, and it is likely to lose case feature information included in a covered region, resulting in difficulty in protecting the privacy of the ophthalmic patient without affecting doctor's diagnosis.

SUMMARY

The present disclosure provides a method and an apparatus for protecting privacy of an ophthalmic patient and a storage medium, to resolve a technical problem that in an existing method for protecting the privacy of the ophthalmic patient, identification information in an uncovered region cannot be removed, and it is likely to lose case feature information included in a covered region, resulting in difficulty in protecting the privacy of the ophthalmic patient without affecting doctor's diagnosis.

A first embodiment of the present disclosure provides a method for protecting privacy of an ophthalmic patient, the method including:

acquiring an examination video of the ophthalmic patient;

extracting image features of each frame of images in the examination video, performing region division on each frame of the images according to position information of organs in the image features, and obtaining a region to be precisely reconstructed and a region to be roughly reconstructed according to a region division result;

performing three-dimensional (3D) reconstruction on the region to be precisely reconstructed and the region to be roughly reconstructed, to obtain 3D reconstruction data corresponding to each frame of the images; and rendering all the 3D reconstruction data into a 3D reconstruction video.

Further, the acquiring an examination video of the ophthalmic patient includes:

acquiring an alternate cover test video and a cover-uncover test video of a strabismus patient at a preset examination distance;

acquiring an ocular motility video of a patient with thyroid-associated ophthalmopathy (TAO), measurements of the ocular motility video are taken in the nine diagnostic positions of gaze;

selecting a corresponding examination distance according to an age group of a nystagmus patient, and acquiring a primary position (fixating straight) video of the nystagmus patient according to the examination distance; and acquiring a video of measurement of levator excursion (downgaze and upgaze) of a patient with ptosis.

Further, the performing 3D reconstruction on the region to be precisely reconstructed and the region to be roughly reconstructed, to obtain 3D reconstruction data corresponding to each frame of the images specifically includes:

constructing a discrete constraint item according to a discrete feature in the image features, constructing a continuous constraint item according to a continuous feature in the image features, and combining the discrete constraint item and the continuous constraint item into a nonlinear optimization problem;

determining parameters of a 3D reconstruction model by solving the nonlinear optimization problem;

solving a first parameter for reconstructing the region to be precisely reconstructed, from the parameters, and solving a second parameter for reconstructing the region to be roughly reconstructed, from the parameters; and performing a matrix vector operation according to a basis of the 3D reconstruction model, the first parameter, and the second parameter, to obtain the 3D reconstruction data corresponding to each frame of the images.

Further, the performing 3D reconstruction on the region to be precisely reconstructed and the region to be roughly reconstructed, to obtain 3D reconstruction data corresponding to each frame of the images further includes:

performing occlusion detection on each frame of the images in the examination video by using a pre-trained neural network, to obtain an occlusion detection result of each frame of the images; and using 3D reconstruction data of a previous frame as 3D reconstruction data of a current frame when the occlusion detection result is bilateral occlusion.

Further, the performing 3D reconstruction on the region to be precisely reconstructed and the region to be roughly reconstructed, to obtain 3D reconstruction data corresponding to each frame of the images further includes:

transferring a deformation state of an eyebrow region from a face model to the 3D reconstruction data by using a deformation transfer technology.

Further, the rendering the 3D reconstruction data into a 3D reconstruction video specifically includes:

rendering the 3D reconstruction data of each frame of the images into a corresponding two-dimensional (2D) image under a preset condition, and performing image synthesis processing on the 2D images to obtain the 3D reconstruction video.

Further, the preset condition includes a preset virtual camera and a lighting environment.

A second embodiment of the present disclosure provides an apparatus for protecting privacy of an ophthalmic patient, the apparatus including:

a video acquisition module, configured to acquire an examination video of the ophthalmic patient;

a region division module, configured to extract image features of each frame of images in the examination video, perform region division on each frame of the images according to position information of organs in the image features, and obtain a region to be precisely reconstructed and a region to be roughly reconstructed according to a region division result;

a 3D reconstruction module, configured to perform 3D reconstruction on the region to be precisely reconstructed and the region to be roughly reconstructed, to obtain 3D reconstruction data corresponding to each frame of the images; and a data rendering module, configured to render all the 3D reconstruction data into a 3D reconstruction video.

A third embodiment of the present disclosure provides a computer-readable storage medium, where the computer-readable storage medium includes a stored computer program, and when being run, the computer program controls a device in which the computer-readable storage medium is located to perform the method for protecting privacy of an ophthalmic patient described above.

In this embodiment of the present disclosure, each frame of the images is divided into a plurality of image regions according to the position information, and a region to be precisely reconstructed and a region to be roughly reconstructed are then obtained in the image regions in combination with case features required for a disease of an ophthalmic patient, so that when 3D face reconstruction with different precision is subsequently performed according to the region to be precisely reconstructed and the region to be roughly reconstructed, most of identification features of the ophthalmic patient can be covered while reserving most of case features of the ophthalmic patient, thereby protecting privacy of the ophthalmic patient without affecting doctor's diagnosis.

DETAILED DESCRIPTION

The following clearly and completely describes the technical solutions in embodiments of this application with reference to the accompanying drawings in the embodiments of this application. Apparently, the described embodiments are merely some of the embodiments of this application rather than all of the embodiments. All other embodiments obtained by a person of ordinary skill in the art based on the embodiments of this application without creative efforts shall fall within the protection scope of this application.

In the description of this application, it should be understood that terms such as "first" and "second" are used merely for a descriptive purpose, and should not be construed as indicating or implying a relative importance, or implicitly indicating the number of indicated technical features. Thus, features defined with "first" and "second" may explicitly or implicitly include one or more of the features. In the description of this application, unless otherwise specified, "a plurality of" means two or more.

In the description of the utility model, it should be noted that, unless otherwise clearly specified, meanings of terms "install", "connected with", and "connected to" should be understood in a broad sense. For example, the connection may be a fixed connection, a removable connection, or an integral connection; may be a mechanical connection or an electrical connection; may be a direct connection or an indirect connection by using an intermediate medium; or may be intercommunication between two components. Persons of ordinary skill in the art may understand specific meanings of the foregoing terms in the present disclosure based on a specific situation.

Figure 1:
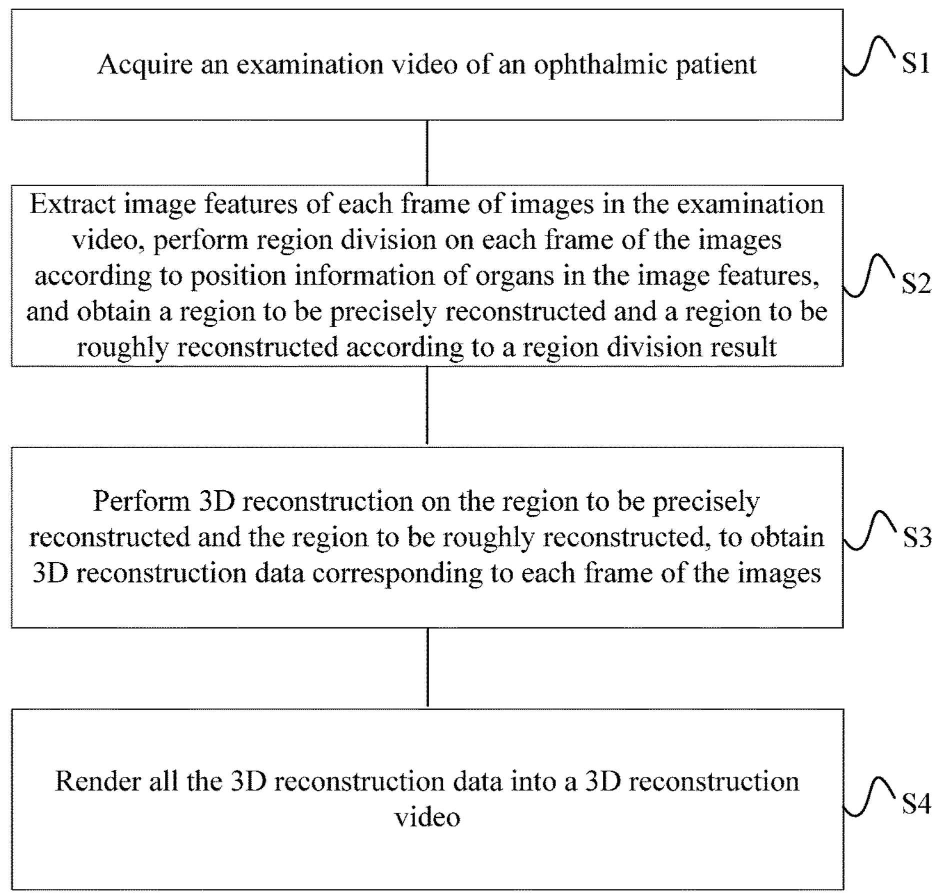
FIG. 1 is a schematic flowchart of a method for protecting privacy of an ophthalmic patient according to an embodiment of the present disclosure.

Referring to FIG. 1, in a first embodiment of the present disclosure, a method for protecting privacy of an ophthalmic patient is provided, the method including the following steps:

S1. Acquire an examination video of an ophthalmic patient.

In this embodiment of the present disclosure, the ophthalmic patients include a strabismus patient, a patient with thyroid-associated ophthalmopathy (TAO), a nystagmus patient, a patient with ptosis, and the like. The examination video may be obtained when pathological features of a patient are acquired by using a camera device, where the examination video is generally a color video, and the examination video includes the pathological features and non-pathological features of a face.

S2. Extract image features of each frame of images in the examination video, perform region division on each frame of the images according to position information of organs in the image features, and obtain a region to be precisely reconstructed and a region to be roughly reconstructed according to a region division result.

In this embodiment of the present disclosure, image features in each frame of the images are automatically extracted by using a pre-trained neural network. The image features include position information of organs of a face, such as position information of eyes, position information of eyebrows, position information of a nose, and position information of a mouth. In this embodiment of the present disclosure, each frame of the images is divided into a plurality of image regions according to the position information, and a region to be precisely reconstructed and a region to be roughly reconstructed are then obtained in the image regions in combination with case features required for a disease of an ophthalmic patient. It should be noted that the region to be precisely reconstructed includes main pathological features for diagnosing an ophthalmic disease, mainly including morphology and motion features of eyeballs and eyelids. The region to be roughly reconstructed includes features that are not related to the eye disease and identification features that are less related to the eye disease, such as a nose and a mouth. In this embodiment of the present disclosure, a region to be precisely reconstructed and a region to be roughly reconstructed are obtained according to the region division result, so that when three-dimensional (3D) face reconstruction with different precision is subsequently performed according to the region to be precisely reconstructed and the region to be roughly reconstructed, most of identification features of the ophthalmic patient can be covered while reserving most of case features of the ophthalmic patient, thereby protecting the privacy of the ophthalmic patient without affecting doctor's diagnosis.

S3. Perform 3D reconstruction on the region to be precisely reconstructed and the region to be roughly reconstructed, to obtain 3D reconstruction data corresponding to each frame of the images.

In this embodiment of the present disclosure, during 3D reconstruction, for the region to be precisely reconstructed, a parameter of a 3D reconstruction model with relatively high precision is solved; for the region to be roughly reconstructed, a parameter of the 3D reconstruction model with relatively low precision is solved; and a matrix vector operation is performed on a basis of the 3D reconstruction model and the parameters obtained through solving, to output 3D reconstruction data of each frame of the images. The basis of the 3D reconstruction model may be a template of the 3D reconstruction model with different semantics but the same topology, different 3D reconstruction data may be formed through linear combination with each other, and the matrix vector operation may be a matrix vector multiplication operation.

S4. Render all the 3D reconstruction data into a 3D reconstruction video.

In this embodiment of the present disclosure, the 3D reconstruction data may be rendered into a 3D reconstruction video by using a renderer for a doctor to make a diagnosis. During reconstruction of the whole video, the doctor can see only the 3D reconstruction video obtained through rendering instead of the examination video. That is, during this process, most of face features, name information, and the like of the patient are not seen by the doctor, thereby effectively protecting the privacy of the ophthalmic patient.

In an embodiment, the acquiring an examination video of the ophthalmic patient includes:

- acquiring an alternate cover test video and a cover-uncover test video of a strabismus patient at a preset examination distance, where the preset examination distance is determined according to a requirement of a doctor;
- acquiring an ocular motility video of a patient with TAO, measurements of the ocular motility video are taken in the nine diagnostic positions of gaze, where the preset examination distance is determined according to a requirement of a doctor;
- selecting a corresponding examination distance according to an age group of a nystagmus patient, and acquiring a primary position (fixating straight) video of the nystagmus patient according to the examination distance, where the corresponding examination distance is determined according to a requirement of a doctor; and
- acquiring a video of measurement of levator excursion (downgaze and upgaze) of a patient with ptosis, where the preset examination distance is determined according to a requirement of a doctor.

In this embodiment of the present disclosure, a device for acquiring the examination video may be at least one of a camera, a video camera, and a mobile terminal, and all the acquired examination videos are color videos, to improve the accuracy of feature extraction.

In an embodiment, the performing 3D reconstruction on the region to be precisely reconstructed and the region to be roughly reconstructed, to obtain 3D reconstruction data corresponding to each frame of the images specifically includes:

- constructing a discrete constraint item according to a discrete feature in the image features, constructing a continuous constraint item according to a continuous feature in the image features, and combining the discrete constraint item and the continuous constraint item into a nonlinear optimization problem;
- determining parameters of a 3D reconstruction model by solving the nonlinear optimization problem, where the parameters specifically include a set of shape parameters and a set of motion parameters; and
- solving a first parameter for reconstructing the region to be precisely reconstructed, from the parameters, and solving a second parameter for reconstructing the region to be roughly reconstructed, from the parameters.

In this embodiment of the present disclosure, the first parameter is a parameter with relatively high precision, and the second parameter is a parameter with relatively low precision. The first parameter is used for performing precise reconstruction on the region to be precisely reconstructed, and the second parameter is used for performing rough reconstruction on the region to be roughly reconstructed.

A matrix vector operation is performed according to a basis of the 3D reconstruction model, the first parameter, and the second parameter, to obtain the 3D reconstruction data corresponding to each frame of the images.

In an embodiment, the performing 3D reconstruction on the region to be precisely reconstructed and the region to be roughly reconstructed, to obtain 3D reconstruction data corresponding to each frame of the images further includes:

- performing occlusion detection on each frame of the images in the examination video by using a pre-trained neural network, to obtain an occlusion detection result of each frame of the images.

In a specific implementation, the occlusion detection result includes four types, namely, left occlusion, right occlusion, bilateral occlusion, and no occlusion.

3D reconstruction data of a previous frame is used as 3D reconstruction data of a current frame when the occlusion detection result is the bilateral occlusion.

When a case in which there is the bilateral occlusion in the image is detected, to avoid error reconstruction caused by unreliable image features, 3D reconstruction data of a previous frame is used as 3D reconstruction data of a current frame. For example, in an alternate cover test of strabismus, an eye region is occluded in the case of the bilateral occlusion, but image features in the occluded region are unreliable.

In an embodiment, the performing 3D reconstruction on the region to be precisely reconstructed and the region to be roughly reconstructed, to obtain 3D reconstruction data corresponding to each frame of the images further includes:

- transferring a deformation state of an eyebrow region from a face model to the 3D reconstruction data by using a deformation transfer technology. The deformation transfer technology includes a Laplace deformation technology and a triangular mesh deformation transfer technology.

When the ophthalmic patient suffers from a TAO, in an ocular motility video of the TAO, measurements of the ocular motility video are taken in the nine diagnostic positions of gaze, motion of eyebrows is beneficial to diagnosis of the TAO. In this embodiment of the present disclosure, a deformation state of an eyebrow region is transferred from a face model to final 3D reconstruction data by using a deformation transfer technology, which can effectively reserve case features of the TAO, and can also protect the privacy of the patient without affecting doctor's diagnosis.

In an embodiment, the rendering the 3D reconstruction data into a 3D reconstruction video specifically includes:

rendering the 3D reconstruction data of each frame of the images into a corresponding 2D image under a preset condition, and performing image synthesis processing on the 2D images to obtain the 3D reconstruction video.

In an embodiment, the preset condition includes a preset virtual camera and a lighting environment.

The following beneficial effects are included during implementation of the embodiments of the present disclosure:

Advantage 1: In this embodiment of the present disclosure, only a few of identification features are reserved while most of pathological features are reserved, thereby effectively protecting privacy of an ophthalmic patient without affecting doctor's diagnosis. Through clinician tests, the embodiments of the present disclosure have good performance in four common ophthalmic diseases involving an eye appearance, and can meet daily diagnosis requirements, including ptosis, nystagmus, strabismus, and TAO; and different from conventional manners of photo coverage and cutting, identification of the patient in a 3D reconstruction video finally obtained in this embodiment of the present disclosure cannot be identified by relatives and friends of the patient, and an original face image cannot be restored either by using the 3D reconstruction video finally obtained in this embodiment of the present disclosure, thereby further protecting the privacy of the patient.

Advantage 2: The embodiments of the present disclosure have a simple requirement for a device, and only require an input single-view color video, instead of a depth camera or a multi-view color camera array.

Advantage 3: Different from conventional two-dimensional (2D) planar image processing, the 3D reconstruction video in this embodiment of the present disclosure can reserve more disease features.

Advantage 4: Statistical analysis shows that the embodiments of the present disclosure can effectively improve the willingness of the patient to cooperate in collecting eye appearance image information, thereby facilitating the improvement of medical records and implementing long-term follow-up of a patient's condition.

Advantage 5: Medical face image information is always unstructured data, and the 3D reconstruction video obtained through digital processing in this embodiment of the present disclosure is beneficial to the standardization and structural unification of medical information, and is beneficial to clinical research and the development of a new medical artificial intelligence system.

Figure 2:
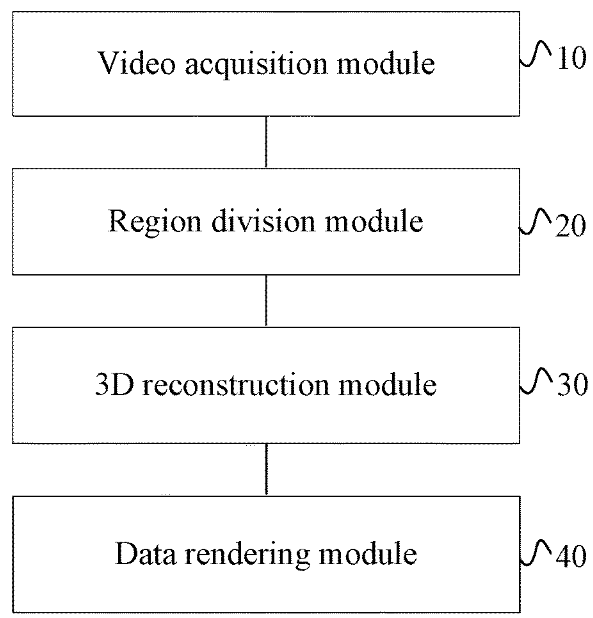
FIG. 2 is a schematic structural diagram of an apparatus for protecting privacy of an ophthalmic patient according to an embodiment of the present disclosure.

Referring to FIG. 2, an embodiment of the present disclosure provides an apparatus for protecting privacy of an ophthalmic patient, the apparatus including:

a video acquisition module 10, configured to acquire an examination video of the ophthalmic patient;

a region division module 20, configured to extract image features of each frame of images in the examination video, perform region division on each frame of the images according to position information of organs in the image features, and obtain a region to be precisely reconstructed and a region to be roughly reconstructed according to a region division result;

a 3D reconstruction module 30, configured to perform 3D reconstruction on the region to be precisely reconstructed and the region to be roughly reconstructed, to obtain 3D reconstruction data corresponding to each frame of the images; and a data rendering module 40, configured to render all the 3D reconstruction data into a 3D reconstruction video.

Further, the video acquisition module 10 is specifically configured to:

acquire an alternate cover test video and a cover-uncover test video of a strabismus patient at a preset examination distance;

acquire an ocular motility video of a patient with TAO, measurements of the ocular motility video are taken in the nine diagnostic positions of gaze;

select a corresponding examination distance according to an age group of a nystagmus patient, and acquire a primary position (fixating straight) video of the nystagmus patient according to the examination distance; and acquire a video of measurement of levator excursion (downgaze and upgaze) of a patient with ptosis.

Further, the 3D reconstruction module 30 is specifically configured to:

construct a discrete constraint item according to a discrete feature in the image features, construct a continuous constraint item according to a continuous feature in the image features, and combine the discrete constraint item and the continuous constraint item into a nonlinear optimization problem;

determine parameters of a 3D reconstruction model by solving the nonlinear optimization problem;

solve a first parameter for reconstructing the region to be precisely reconstructed, from the parameters, and solve a second parameter for reconstructing the region to be roughly reconstructed, from the parameters; and perform a matrix vector operation according to a basis of the 3D reconstruction model, the first parameter, and the second parameter, to obtain the 3D reconstruction data corresponding to each frame of the images.

Further, the 3D reconstruction module 30 is further configured to:

perform occlusion detection on each frame of the images in the examination video by using a pre-trained neural network, to obtain an occlusion detection result of each frame of the images; and use 3D reconstruction data of a previous frame as 3D reconstruction data of a current frame when the occlusion detection result is bilateral occlusion.

Further, the 3D reconstruction module 30 is further configured to:

transfer a deformation state of an eyebrow region from a face model to the 3D reconstruction data by using a deformation transfer technology.

Further, the data rendering module 40 is specifically configured to:

render the 3D reconstruction data of each frame of the images into a corresponding 2D image under a preset condition, and perform image synthesis processing on the 2D images to obtain the 3D reconstruction video.

Further, the preset condition includes a preset virtual camera and a lighting environment.

An embodiment of the present disclosure provides a computer-readable storage medium, where the computer-readable storage medium includes a stored computer program, and when being run, the computer program controls a device in which the computer-readable storage medium is located to perform the method for protecting privacy of an ophthalmic patient described above.

The above descriptions are merely preferred implementations of the present disclosure. It should be noted that a person of ordinary skill in the art may further make several improvements and refinements without departing from the principle of the present disclosure, but such improvements and refinements are also deemed as falling within the protection scope of the present disclosure.

The invention claimed is:

1. A method for protecting privacy of an ophthalmic patient, wherein the method comprises:

acquiring an examination video of the ophthalmic patient;

extracting image features of each frame of images in the examination video, performing region division on each frame of the images according to position information of organs in the image features, and obtaining a region to be precisely reconstructed and a region to be roughly reconstructed according to a region division result;

performing three-dimensional (3D) reconstruction on the region to be precisely reconstructed and the region to be roughly reconstructed, to obtain 3D reconstruction data corresponding to each frame of the images;

rendering all the 3D reconstruction data into a 3D reconstruction video; and wherein the acquiring an examination video of the ophthalmic patient comprises:

acquiring an alternate cover test video and a cover-uncover test video of a strabismus patient at a preset examination distance;

acquiring an ocular motility video of a patient with thyroid-associated ophthalmopathy (TAO), measurements of the ocular motility video are taken in the nine diagnostic positions of gaze;

selecting a corresponding examination distance according to an age group of a nystagmus patient, and acquiring a primary position (fixating straight) video of the nystagmus patient according to the examination distance; and acquiring a video of measurement of levator excursion (downgaze and upgaze) of a patient with ptosis.

2. The method for protecting privacy of an ophthalmic patient according to claim 1, wherein the performing 3D reconstruction on the region to be precisely reconstructed and the region to be roughly reconstructed, to obtain 3D reconstruction data corresponding to each frame of the images specifically comprises:

constructing a discrete constraint item according to a discrete feature in the image features, constructing a continuous constraint item according to a continuous feature in the image features, and combining the discrete constraint item and the continuous constraint item into a nonlinear optimization problem;

determining parameters of a 3D reconstruction model by solving the nonlinear optimization problem;

solving a first parameter for reconstructing the region to be precisely reconstructed, from the parameters, and solving a second parameter for reconstructing the region to be roughly reconstructed, from the parameters; and performing a matrix vector operation according to a basis of the 3D reconstruction model, the first parameter, and the second parameter, to obtain the 3D reconstruction data corresponding to each frame of the images.

3. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 2.

4. The method for protecting privacy of an ophthalmic patient according to claim 1, wherein the performing 3D reconstruction on the region to be precisely reconstructed and the region to be roughly reconstructed, to obtain 3D reconstruction data corresponding to each frame of the images further comprises:

performing occlusion detection on each frame of the images in the examination video by using a pre-trained neural network, to obtain an occlusion detection result of each frame of the images; and using 3D reconstruction data of a previous frame as 3D reconstruction data of a current frame when the occlusion detection result is bilateral occlusion.

5. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 4.

6. The method for protecting privacy of an ophthalmic patient according to claim 1, wherein the performing 3D reconstruction on the region to be precisely reconstructed and the region to be roughly reconstructed, to obtain 3D reconstruction data corresponding to each frame of the images further comprises:

transferring a deformation state of an eyebrow region from a face model to the 3D reconstruction data by using a deformation transfer technology.

7. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 6.

8. The method for protecting privacy of an ophthalmic patient according to claim 1, wherein the rendering the 3D reconstruction data into a 3D reconstruction video specifically comprises:

rendering the 3D reconstruction data of each frame of the images into a corresponding two-dimensional (2D) image under a preset condition, and performing image synthesis processing on the 2D images to obtain the 3D reconstruction video.

9. The method for protecting privacy of an ophthalmic patient according to claim 8, wherein the preset condition comprises a preset virtual camera and a lighting environment.

10. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 9.

11. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 8.

12. A non-transitory computer-readable storage medium, wherein the computer-readable storage medium comprises a stored computer program, and when being run, the computer program controls a device in which the computer-readable storage medium is located to perform the method for protecting privacy of an ophthalmic patient according to claim 1.

13. A non-transitory apparatus for protecting privacy of an ophthalmic patient, wherein the apparatus comprises:

a video acquisition module, configured to acquire an examination video of the ophthalmic patient;

a region division module, configured to extract image features of each frame of images in the examination video, perform region division on each frame of the images according to position information of organs in the image features, and obtain a region to be precisely reconstructed and a region to be roughly reconstructed according to a region division result;

a 3D reconstruction module, configured to perform 3D reconstruction on the region to be precisely reconstructed and the region to be roughly reconstructed, to obtain 3D reconstruction data corresponding to each frame of the images;

a data rendering module, configured to render all the 3D reconstruction data into a 3D reconstruction video; and wherein the acquiring an examination video of the ophthalmic patient comprises:

acquiring an alternate cover test video and a cover-uncover test video of a strabismus patient at a preset examination distance;

acquiring an ocular motility video of a patient with thyroid-associated ophthalmopathy (TAO), measurements of the ocular motility video are taken in the nine diagnostic positions of gaze;

selecting a corresponding examination distance according to an age group of a nystagmus patient, and acquiring a primary position (fixating straight) video of the nystagmus patient according to the examination distance; and acquiring a video of measurement of levator excursion (downgaze and upgaze) of a patient with ptosis.

* * * * *